United States Patent
Hansen et al.

[11] Patent Number: 5,928,280
[45] Date of Patent: Jul. 27, 1999

[54] EXPANDABLE ENDOVASCULAR STENT

[75] Inventors: Palle M. Hansen, Roskilde, Denmark; Zaza A. Kavteladze, Moscow, Russian Federation

[73] Assignee: William Cook Europe A/S, Bjaeverskov, Denmark

[21] Appl. No.: 08/711,048

[22] Filed: Sep. 10, 1996

[30] Foreign Application Priority Data

Sep. 11, 1995 [DK] Denmark ................ 0995/95

[51] Int. Cl.$^6$ .................................. A61F 2/06
[52] U.S. Cl. ................... 623/1; 623/12; 600/36
[58] Field of Search ................. 623/1, 11, 12; 606/191, 194, 195, 198; 600/36

[56] References Cited

U.S. PATENT DOCUMENTS

| | | | |
|---|---|---|---|
| 4,856,516 | 8/1989 | Hillstead | 623/1 |
| 5,102,417 | 4/1992 | Palmaz | 623/11 |
| 5,344,426 | 9/1994 | Lau et al. . | |
| 5,354,308 | 10/1994 | Simon et al. | 606/198 |
| 5,370,683 | 12/1994 | Fontaine . | |
| 5,395,390 | 3/1995 | Simon et al. | 623/1 |
| 5,397,355 | 3/1995 | Marin et al. | 623/12 |
| 5,449,373 | 9/1995 | Pinchasik et al. . | |
| 5,496,365 | 3/1996 | Srgo | 623/1 |
| 5,562,697 | 10/1996 | Christiansen | 623/1 |
| 5,591,197 | 1/1997 | Orth et al. | 623/1 |
| 5,593,442 | 1/1997 | Klein | 623/1 |
| 5,630,829 | 5/1997 | Lauterjung | 606/198 |

FOREIGN PATENT DOCUMENTS

| | | |
|---|---|---|
| 0221570 | 1/1991 | European Pat. Off. . |
| 0423916 | 4/1991 | European Pat. Off. . |
| 0480667 | 4/1992 | European Pat. Off. . |
| 0556850 | 8/1993 | European Pat. Off. . |
| 0566807 | 10/1993 | European Pat. Off. . |
| 0622088 | 11/1994 | European Pat. Off. . |
| 0645125 | 3/1995 | European Pat. Off. . |
| 0669114 | 8/1995 | European Pat. Off. . |
| 3918736 | 12/1990 | Germany . |
| 3342798 | 10/1992 | Germany . |
| 4303181 | 8/1994 | Germany . |
| 9216166 | 10/1992 | WIPO . |
| 9313825 | 7/1993 | WIPO . |
| 9403127 | 2/1994 | WIPO ............ 623/1 |
| 9412136 | 6/1994 | WIPO . |
| 9417754 | 8/1994 | WIPO ............ 623/1 |
| 9503010 | 2/1995 | WIPO ............ 623/1 |
| 9531945 | 11/1995 | WIPO . |
| 9614028 | 5/1996 | WIPO . |

OTHER PUBLICATIONS

Cook–Z® Stents, "Gianturco–Rösch Covered Esophageal Design", William Cook Europe.

Cook–Z™ Stents, "Gianturco–Rösch Biliary Design", Cook Incorporated 1989.

*Primary Examiner*—Michael J. Milano
*Assistant Examiner*—Tram Anh T. Nguyen
*Attorney, Agent, or Firm*—Richard J. Godlewski

[57] ABSTRACT

An expandable endovascular stent comprises a flexible, tubular body (1) with a longitudinal axis, the wall of which is formed by interconnected, closed frame cells (2) arranged with at least two cells adjacent to each other in the circumferential direction. Filament-shaped frame material capable of transmitting compressive forces in the axial direction of the filament extends continuously from one frame cell directly into the frame cell following in the longitudinal direction. The stent can be expanded from a radially compressed state into a state having a larger diameter. In the expanded state of the stent, the pressure transmitting frame material in several of the frame cells (2) forms a heart-like or arrowhead-like shape with two interconnected shorter cell sides (5) positioned opposite to and interconnected with two mutually converging longer cell sides (3).

20 Claims, 6 Drawing Sheets

EXPANDABLE ENDOVASCULAR STENT

TECHNICAL FIELD

The present invention relates generally to medical devices and, particularly, to an expandable endovascular stent.

BACKGROUND OF THE INVENTION

One expandable endovascular stent is known from German patent No. 33 42 798, where the frame cells are formed by sets of wires extending helically through the body at opposite winding directions. The frame cells are rhomboidal, and the stent length changes substantially at the expansion, which gives rise to several disadvantages, one being that it is difficult to position the stent accurately, another that the insertion system is complicated.

U.S. Pat. No. 5,370,683 describes a stent formed from a single filament which is wrapped around a mandril in a wavy course having alternating short and long, elongated pieces of filament, whereupon the filament is arranged in a helical course with the wave troughs mutually aligned. Then the wave troughs have been interconnected to form rhomboidal frame cells having a pair of opposite short cell sides and another pair of opposite long cell sides. Among other things, this stent is distinguished in being capable of compression into a radially compressed state without the stent ends having to be pulled apart. The stent can be arranged in a catheter in a radially compressed state and be inserted and positioned at the desired site in a lumen, such as a blood vessel, whereupon the catheter can be pulled away and the stent be expanded by means of an inflatable balloon arranged inside the stent. It is a disadvantage of the stent that it has relatively poor bending flexibility, as this reduces the adaptability of the stent to the supported, flexible vessel. Nor is it an advantage that the cells of the stent are relatively open and thus more exposed to fibrous in-growth into the inner lumen of the stent.

In a stent known from EP-A 645125 a tubular stent body is also formed from a single angularly bent filament wound in a spiral shape with the apexes hooked into each other to form rhomboidal cells. Because the apexes are only hooked into each other, there is a risk of compression of the stent in the longitudinal direction if it is pushed out of the catheter. The two ends of the filament are returned through the stent body in a spiral course, but do not remove the risk of longitudinal changes in the part of the stent which is expanding outside the end of the catheter. It may, therefore, be necessary to pull the stent out of the catheter by means of a pulling device passing centrally through the stent body and restricting its compression inside the catheter. The flexibility of the stent at bending is also relatively poor, and the cells are very open.

A number of different stents of another type is also known, in which the cell material does not continue directly from one frame cell to the following one in the longitudinal direction. Instead, this type of stents is constructed from several Z-shape-bent wires joined into a tubular body by means of connecting threads or being hooked into each other, vide EP-A 622088, EP-A 480667, WO93/13825 and EP-A 556850. All these stents are of limited bending flexibility and some of them are very complicated to manufacture. The connecting threads for joining the Z-bent, resilient frame material limit the expanded stent diameter, but yield completely to axial pressure. This results in the substantial disadvantage that impacts on a cell are not transferred to the cell following in the longitudinal direction, so that the stent has discontinuous properties, can open up and will exhibit breaks at bending.

Stents constructed from wires wound about each other to form closed cells are known from DE-A 39 18 736, where the cells are elongated or Ω-shaped, and from WO94/03127, where the cells are oval in the circumferential direction.

SUMMARY OF THE INVENTION

The foregoing problems are solved and a technological advantage is achieved in an expandable endovascular stent comprising a flexible, tubular body with a longitudinal axis, the wall of which is formed by interconnected, closed frame cells arranged with at least two cells adjacent to each other in the circumferential direction, the frame cells having at least two elongated, mutually converging cell sides, the body including filament-shaped frame material capable of transmitting compressive forces in the axial direction of the filament extending continuously from one frame cell directly into the frame cell following in the longitudinal direction, which stent is expandable from a radially compressed state into a state having a larger diameter.

The object of the invention is to provide a stent which can be compressed and expanded radially without any substantial change of the length of the body, and which has a frame structure providing the stent with a higher, uniform bending flexibility and thus higher vascular adaptability. It is furthermore an object that the stent also has a compressive strength which is suitably high and adapted to the application in question.

In view of this, the stent according to the present invention is characterized in that in the expanded state of the stent, the pressure transmitting frame material in several of the frame cells forms a heart-like or arrowhead-like shape with two interconnected shorter cell sides positioned opposite and connected with the two mutually converging longer cell sides.

In the heart-like or arrowhead-like shape, the point of interconnection between the two shorter cell sides points towards the point of interconnection between the two longer cell sides of the same cell. Among other things, this provides the considerable advantage that when the center axis of the stent is bent, the cells are deformed on the outer side of the curvature so that the angle facing into the cell between the two shorter cell sides becomes smaller, and the cells become more open with a larger cell length. This may occur at a very small bending moment, because the cells can expand without simultaneous contraction of the surrounding cells. The smaller angle between the shorter cell sides at the same time increases the stresses thereof directed in the circumferential direction and counteracts the reduction of the radial compressive strength of the stent on the outer side of the curvature generated by the lower cell density here. The high bending flexibility of the stent and its ability to maintain considerable radial compressive strength even at a sharp curvature of its longitudinal axis provide the stent with a large vascular compatibility, permit positioning of the stent in areas with vascular curvatures or other vascular variations and presumably counteract long-term damage to the vascular wall caused by the inserted stent.

The many closed cells give the stent evenly distributed uniform properties, and the cell shape or cell shapes are relatively dense, which counteracts re-stenosis or other lumen reduction of the vessel.

At radial compression of the stent, the longer cell sides fold together about the shorter cell sides. At full compression about a guide wire, the stent has a configuration where the cell sides are packed tightly about the longitudinal axis of the stent and extend substantially in parallel with it. This provides an advantageous possibility of positioning the stent in a catheter with a small internal diameter. A stent with a diameter of 8 mm may, for example, be compressed for positioning in a catheter with an internal lumen of 7 French (about 2.3 mm).

With a suitable choice of the stent material, the stent may be self-expanding when the catheter is removed following insertion of the compressed stent. The self-expanding capability is mainly obtained owing to the bending stresses occurring at the bending of the cell sides near their ends. The result of the frame cell shape is that bending normally occurs at six points in the cell contrary to the four points in a rhomboidal cell, and thus the stent can have a more uniform and finer distribution of the expansion forces. Alternatively, or in supplement, the stent may be expanded by means of an inflatable balloon. The self-expanding stent need not be compressed radially about a balloon, and therefore during insertion it may be positioned in a thinner catheter.

At the folding together of the frame cells, the cell sides of a cell are laid down into the neighboring cells without having to displace them in the longitudinal direction of the stent. This means that at the change between the folded together and the expanded state, the stent has substantially unchanged length apart from a negligible change in length at the end of the stent where the cell sides are not laid down into following cells. The stable length is advantageous when positioning the stent, as it can be positioned accurately in the vasoconstriction before release. When the catheter is retracted and the stent is released, the frame cells can expand to their final position in contact with the vascular wall approximately without any longitudinal displacement of the ends of the stent. Therefore, the introducer system may be of a simple design and extremely easy to operate. The only requirement is a pusher which can be held in stationary contact with the end of the compressed stent nearest the insertion opening, while the catheter is retracted. The simple introducer system reduces the risk of erroneous positioning of the stent and is rapid in use.

It is possible to orient the points of the hearts in an oblique angle so that they point along a helical line in the periphery of the body. In consideration of compact compression of the stent, the arrowheads or heart points preferably face in the longitudinal direction of the body, and the interval between two neighboring frame cells with the same orientation of the arrowheads or heart points consists of a frame cell with an opposite orientation of the arrowhead or point. The interconnection between the neighboring cells in this design extends in the longitudinal direction of the stent.

In a preferred embodiment, the frame cells adjacent to each other in an annular row in the circumferential direction of the body have alternatingly oriented arrowheads or heart points and constitute a frame pattern repeated along the length of the body. In this design, the interconnections between adjacent cells in one circumferential row extend in axial extension of the arrowheads or points in the next circumferential row, and all frame cells have the advantageous shape which gives the stent uniform properties, such as uniform torsional, bending and compression rigidities.

The cells may extend in a helical pattern along the length of the body by both the shorter cell sides and also the longer cell sides having mutually different lengths. However, in consideration of the manufacture of the stent, the two shorter cell sides preferably have substantially the same length, and the two longer cell sides have substantially the same length.

The first angle between the two longer cell sides and facing into the cell, together with the number of cells in the circumferential direction of the body, determines the bending rigidity of the body. With the same number of cells in an annular row, a smaller first angle provides a greater distance between the cells in the longitudinal direction and thus greater bending rigidity and a more open frame structure. The first angle may be in the interval of 20–160°. If the first angle is smaller than 20°, the stent can only expand to a slightly larger diameter than the compressed state. If the first angle is larger than 160°, very large changes in diameter may be obtained, but the number of cells in the longitudinal direction becomes unsuitably large. The first angle is preferably in the interval of 60–120°, providing an advantageously high flexibility combined with a suitable number of cells in the longitudinal direction.

Provided that said arrowheads or points do not face in the circumferential direction, the second angle between the two shorter cell sides and facing into the cell influences the compression rigidity of the body, the density of the frame structure and the extra increase of diameter to which the body may be exposed after the normal expansion to a larger diameter. Such an extra diameter increase into an overexpanded state may, for example, be very advantageous if a self-expanding stent has been inserted into a vessel where re-stenosis occurs. Following the re-stenosis diagnosis, an inflatable balloon may be inserted into the stent and inflated to a large diameter without having to remove the stent, the stent merely being overexpanded by the balloon, only to return to its normal shape when the balloon is removed. The possibility of over-expansion can also be used at the insertion of the stent, as the stent may be positioned inside a hard stenosis before balloon dilation thereof. At the subsequent balloon dilation, the stent helps to keep the hardest stenosis area out at the desired diameter when the balloon is removed. This avoids dilation before the stent is positioned. At over-expansion, it is a substantial advantage that the stent does not change its length at the expansion. If the points of the heart-like or arrowhead-like frame cells face in the circumferential direction, the second angle may suitably be at about 180°. If the points face in the longitudinal direction, the second angle should be larger than 184° so that the shorter arms are folded into the cell at compression of the stent. If the second angle is larger than 340°, and the filament is not of a large diameter, compression rigidity is largely absent. Preferably, the second angle is in the interval of 210–320°, which provides a suitable compression rigidity, good density of cells and a possibility of over-expansion into a substantially larger diameter. The angles are chosen taking into account the field of application concerned. The closer the second angle is to 180°, the higher is the compression rigidity of the stent, but if the angle becomes substantially smaller than 210°, the possibilities of over-expansion become less favorable.

In a specially preferred embodiment, the longer cell sides and the shorter cell sides all form an angle of between 10° and 45° with the longitudinal direction of the body. This renders it possible to compress the stent in a simple manner, either manually or by pushing the stent through a funnel-shaped loading sheet. It is particularly advantageous if the longer cell sides form an angle of between 40° and 45° with the longitudinal direction.

It is possible to render the stent more bending flexible in certain areas by said first angle in the frame cells being smaller in one area of the body than in another area of the body. This may be used, for example, to make the stent more flexible in the end areas so that the transition from the stent-affected to the non-affected area of the vascular wall becomes even, whereby the vascular wall is irritated as little as possible at the stent ends, and vascular injuries and tissue in-growth are counteracted. This is particularly advantageous if the risk of stent migration in the vessel is small.

It is also possible to design the stent so that said second angle in the frame cells is larger in one area of the body than in another area of the body, whereby the compressive strength of the stent can be varied according to desire. In case of hard stenoses, the second angle may, for example, be larger at the end areas of the body so that the stent exerts the largest radial pressure at its middle, and the ends are softer and more adaptable to the vessel. It may also be desirable that the stent is fixed in the vessel by exerting a large contact pressure at the end areas, and in this case the second angle is then smaller than at the stent middle.

In some applications, it is desirable for the stent to have a bell or hourglass shape, which can be obtained in that at least one end of the body, the shorter and longer cell sides of the frame cells are of greater length, and/or the frame cells have a smaller angle between the shorter cell sides than at the middle of the body, whereby the body has a larger diameter at the end than at the middle.

With a view to compressing the stent to a configuration with an advantageously small external diameter, it may be advantageous that the number of wires in the stent is not too high. If the stent is to be inserted by means of a catheter with a small diameter, the number of frame cells in an annular row in the circumferential direction of the body preferably substantially corresponds to the radius of the body measured in mm. Substantially in this context means that for each four mm radius, the cell number may be one more or less than the radius measure in mm, for example one cell more or less for a stent having a diameter of 6 mm, two cells more or less for a stent having a diameter of 10 mm, etc.

In a preferred embodiment, the body is formed by several filaments constituting the shorter and the longer cell sides and being wound about each other at the adjacent ends of the pairs of shorter or longer cell sides, preferably so that each filament has a stepped spiral-like or a stepped wave-like course in the longitudinal direction of the body. The winding together of the filaments at the adjacent ends mutually locks the frame cells, but at the same time provides the filaments with an advantageous possibility of bending apart from each other through opening of the windings when the stent is compressed radially, which reduces filament stresses at the points of interconnection. The result of the geometrical locking of the mutual position of the cells provided by the winding about is that in its compressed state the stent has a large axial rigidity so that it can be removed from the catheter without problems and without changes in length, when the catheter is retracted. In its expanded state, the winding about ensures that the stent has a stable shape in which the frame cells do not slide in relation to each other at the application of external loads. The stent manufactured from filaments is relatively simple to manufacture, and the course of the filaments throughout the body can be selected so that the stent is both torsionally stable and pressure stable, for example by the filaments having a spiral-like or wave-shaped course.

Alternatively, the body may be formed from a thin-walled tube or a thin-walled piece of plate in which the cell openings are fashioned, preferably by etching. The frame cells are in this case fashioned in an integral piece of material, which may be done by machining alone. Alternatives to chemical etching or laser etching can be spark machining, laser cutting or punching of the thin-walled material, which are well-known methods for forming holes in such a material.

In case the tubular body is formed of several filaments the tubular body may include cell junctions where pairs of filaments are twisted one turn about each other about a twist axis extending in a first direction and at least one turn about each other about a second twist axis extending at an angle, preferably at approximately 90° to said first direction. This manner of twisting the pairs of filaments at the cell junctions produces a kind of dual locking of the filaments with the result that the tubular body obtains additional stiffness at the cell junctions so that the periphery of the body maintains an even frame surface, also if the two ends of the body are pulled apart. This may be an advantage in case the stent is to be removed from the vessel after the placement therein.

BRIEF DESCRIPTION OF THE DRAWING

Examples of embodiments of the stent according to the invention will now be described in further detail below with reference to the very schematic drawing, in which.

DETAILED DESCRIPTION

In the following description of non-limiting examples of embodiments of the invention, the same reference numerals will be used for elements having the same effect in the different embodiments.

Figure 5:
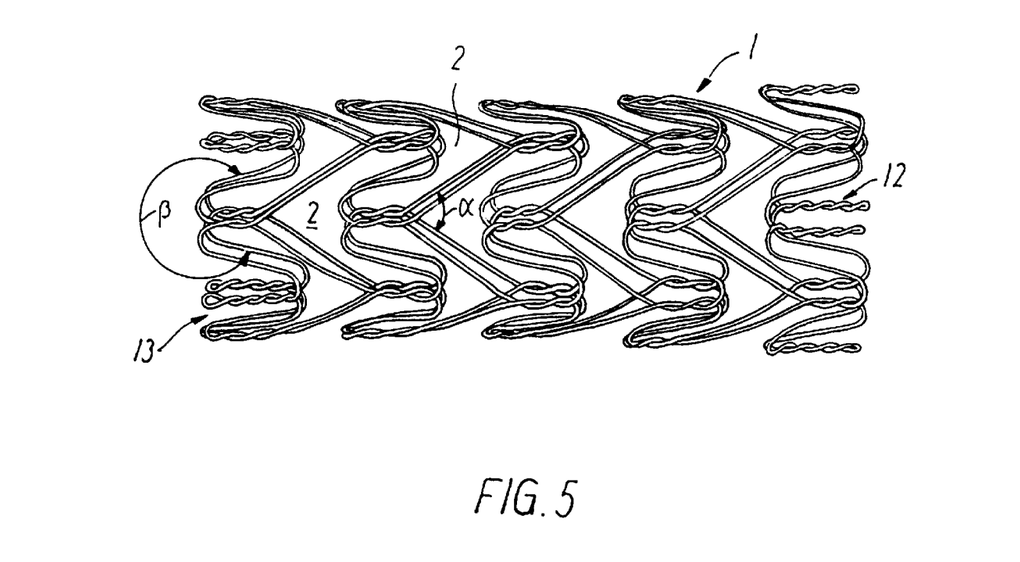
FIG. 5 is a side view of an embodiment of a whole stent according to the invention.

FIG. 5 shows a stent in the form of a tubular body 1 formed of several filaments or wires bent to form heart-shaped frame cells 2 and wound about each other at the places where the cell filaments meet so that the frame cells are fixed to each other both in the longitudinal and the circumferential directions.

Figure 1:
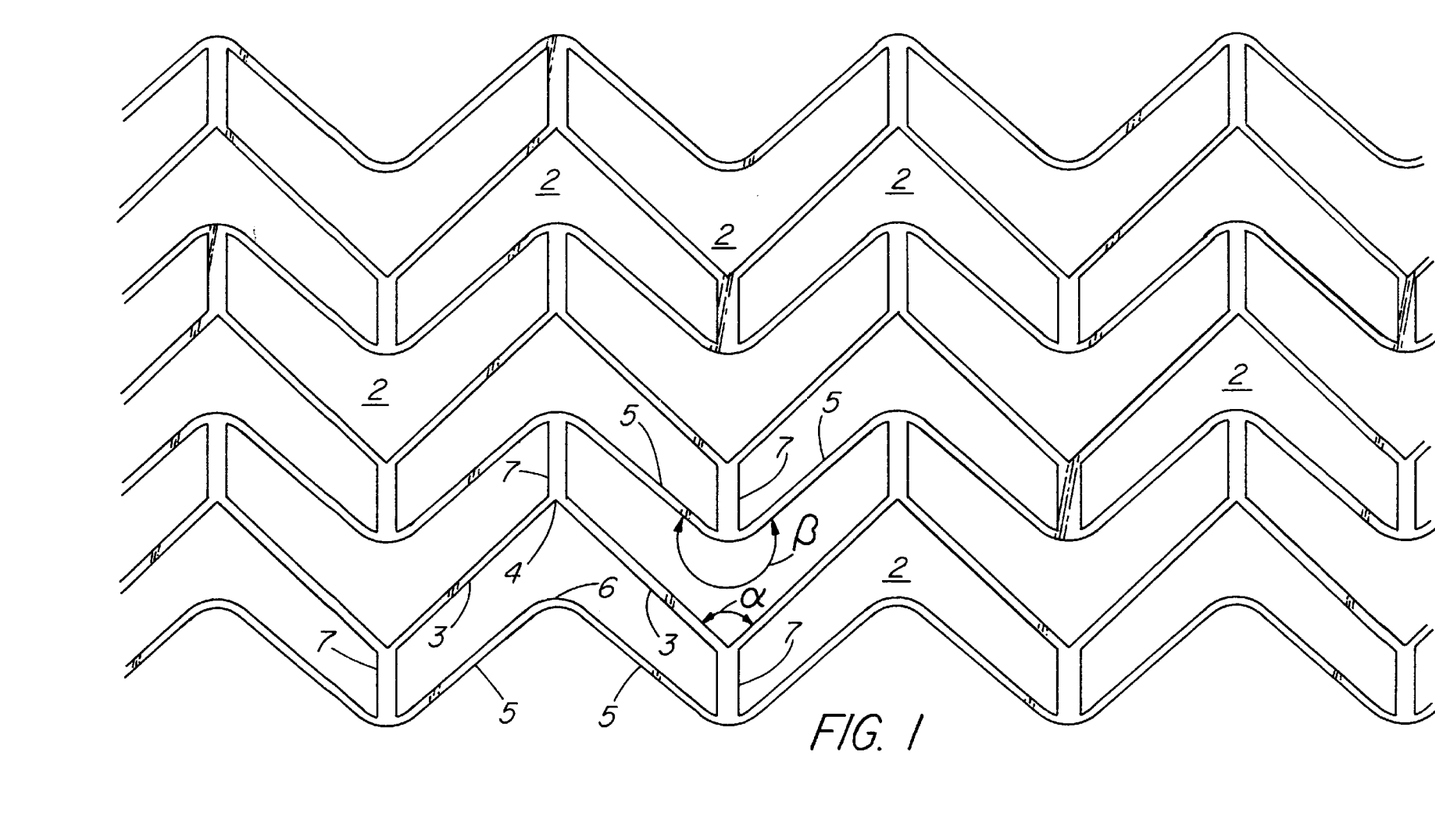
FIG. 1 shows a plane view of an unfolded section of the wall in a stent according to the invention made from thin-walled plate material.

FIG. 1 shows an example of heart-shaped frame cells 2 fashioned in a thin-walled plate made into a tubular shape either before or after the fashioning. The fashioning may be done, for example, by etching or spark machining in a manner known in the art. Each frame cell 2 has two mutually converging longer cell sides 3 converging into a unified filament at the point of the heart and delimiting a first angle α facing into the cell. The frame cell also has two shorter cell sides 5 converging with each other to become unified in a point area positioned opposite the heart point 4. The shorter cell sides delimit a second angle β facing into the cell and they are positioned opposite to the longer cell sides 3, with which they are connected through two side sections 7 to form the closed frame cell of pressure-rigid frame material. The length of the side sections 7 can be made larger or smaller, according to whether the cell is desired to be more or less open, without changing the sizes of the first or the second angle α, β. The shape of the side sections 7 can also be varied; they may, for example, be thinner, have an hourglass shape, I-shape, O-shape or any other shape, but the straight shape shown with a larger thickness than the cell sides 3 and 5 is preferred owing to its simplicity and relatively high rigidity, resulting in the occurrence of any cell deformations mainly in the cell sides 3 and 5. The heart point 4 may be more rounded and the point area 6 may be more pointed or more rounded than shown. It is also possible to insert a connecting section between the two mutually converging cell sides so that the cell shape, for example, becomes more angular without any point areas proper. In the context of the invention, a heart-like or arrowhead-like shape means a closed cell having at one end a tapering shape facing out of the cell, and at the opposite end a more or less tapering shape facing into the cell.

The frame pattern is constructed in such a manner that in the circumferential direction of the body there is an annular row of closed frame cells 2 interconnected by the common side sections 7, and all having their points 4 oriented similarly in the longitudinal direction of the body. The longer cell sides 3 also constitute corresponding sides in an annular adjacent row in the longitudinal direction of the body and consisting of uniformly formed closed frame cells having an opposite orientation of the points 4. These two cell rows constitute a common annular row of cells in which the points 4 have alternatingly opposite orientations and continue into the common side sections in the subsequent row. The stent length can be adapted to the desired application by varying the number of annular rows of cells.

In the preferred embodiment shown, the first angle α is about 90°, and the second angle β is about 263°. This gives the stent advantageously uniform properties, both as to bending and to compressive strength, because the longer cell sides 3 and the shorter cell sides 5 all form an angle of about 45° with the longitudinal direction of the body. At radial compression of the stent, the cell sides are therefore uniformly deformed, and the stresses are distributed evenly between the sides of the cell, which on expansion results in a uniform strong unfolding of all cells with a very low risk of erroneous unfolding and with a uniform resulting pressure influence on the vascular wall. Because the second angle β is smaller than the angle (360°−α) corresponding to a parallel course of the shorter and longer cell sides, the free distance between the point area 6 and the point 4 becomes suitably large so that on compression it can more easily receive the side section 7 from the subsequent frame cell of the same orientation, when it is swung backwards and towards the longitudinal axis of the body. This promotes compact compression of the stent.

Figure 2:
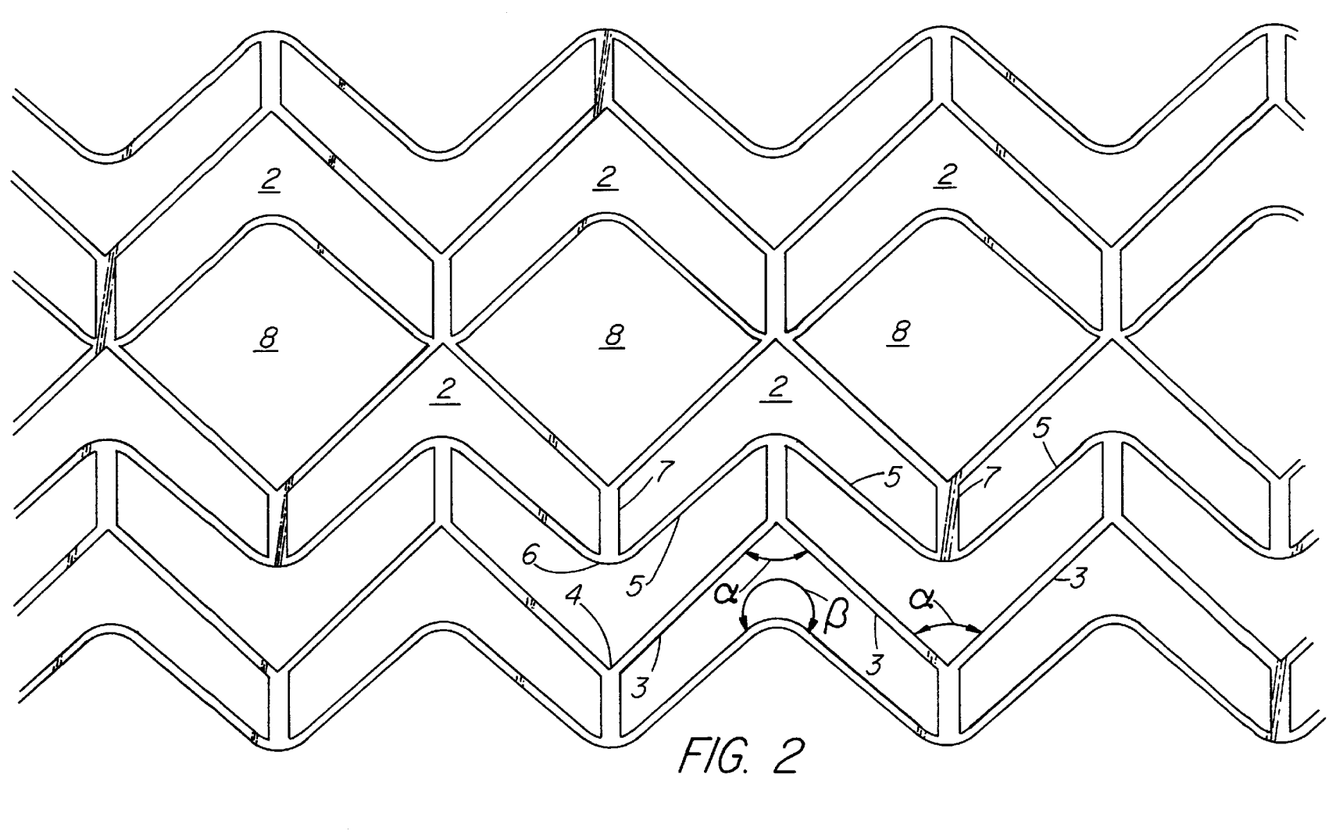
FIG. 2 shows a corresponding view of a second embodiment of the stent.

The embodiment shown in FIG. 2 deviates in that some of the cells do not have the advantageous heart-like or arrowhead-like shape, as a number of rhomboidal cells 8 are inserted in the cell pattern. This gives the stent an area with more open cells and substantially greater bending rigidity, which may, for example, be used for stabilizing undesired large local vascular movements. Naturally, it is also possible to give individual local cells another shape. This may be done in a simple manner by removing one or more cell sides in a cell.

Figure 3:
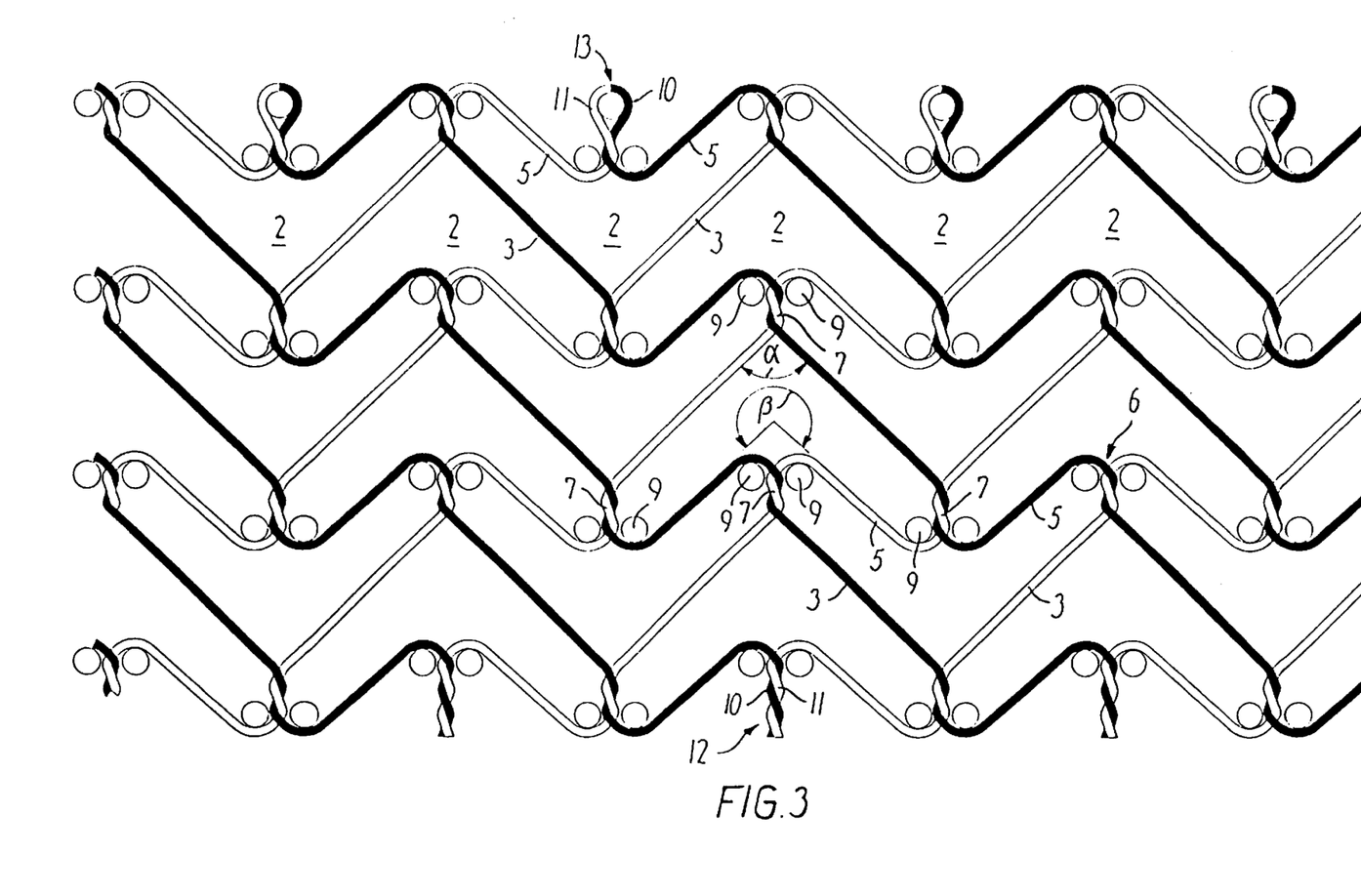
FIG. 3 is a view corresponding to that of FIG. 1 of the most preferred embodiment, in which the frame cells have the same shape as in FIG. 1, and the stent is manufactured from several wound filaments.
Figure 4:
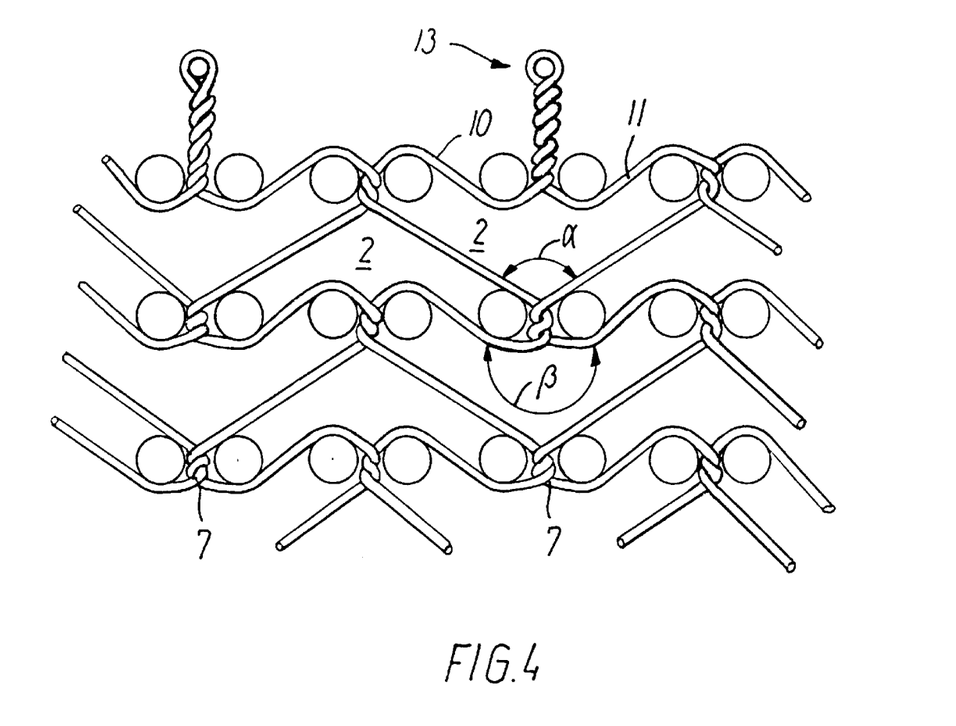
FIG. 4 is a section corresponding to that of FIG. 3 of a stent having a more dense frame structure.

In the embodiment of FIG. 3, the frame cells 2, the first angle α and the second angle β have the same dimensions as in FIG. 1, but the body 1 is formed by filaments bent on a mandril around guide pins 9 and wound once around each other at the side sections 7. Owing to the structure with filaments, the cells have more rounded shapes, and the heart-like shape may assume a heart shape. For each frame cell 2 in a circumferential row, two filaments 10, 11 extend from one end of the stent, which filaments can be wound about each other as a filament end 12 or may continue into each other in an eyelet 13. From the frame cell at the end of the stent, each pair of two filaments 10, 11 extends along the body in a stepped spiral-like course with opposite directions of winding, in which the filaments constitute one of the shorter cell sides 5, are wound about the corresponding filament from the neighboring cell in the same row, continue as the longer cell side 3 in this frame cell, are wound about the second filament of this cell, continue as the shorter cell side 5 in the frame cell in the subsequent row, and so forth until the finish at the other end of the stent. If at even intervals, the filament is wound one half turn more or less about the oppositely extending filament, the filament course is changed from spiral-like into wave-like. The appearance of the frame cells can be changed according to desire by changing the positions and the number of guide pins 9; the cell shape may, for example, be modified within the framework of the description for FIGS. 1 and 2. Endeavors are made to ensure that the longer cell sides 3 and the shorter cell sides 5 have a rectilinear course as far as possible between the curves at the guide pins 9, but in practice, the cell sides may have an S-shaped or any other curved course. FIG. 4 shows an example of a varied cell shape in which the first angle α is about 120°, and the second angle β is about 253°. It is also seen that the side sections 7 are shorter owing to a smaller pitch in the windings. If long side sections are desired, the filaments may be wound several turns about each other. Instead of winding the filaments about each other, the interconnections between the frame cells may be rings or threads locking the two adjacent filaments together. A further cell shape is shown in FIG. 5, where the first angle α is about 70°, and the second angle is about 322°. Such a design may be advantageous if the filament diameter is relatively large and the filament thus less flexible.

Figure 6:
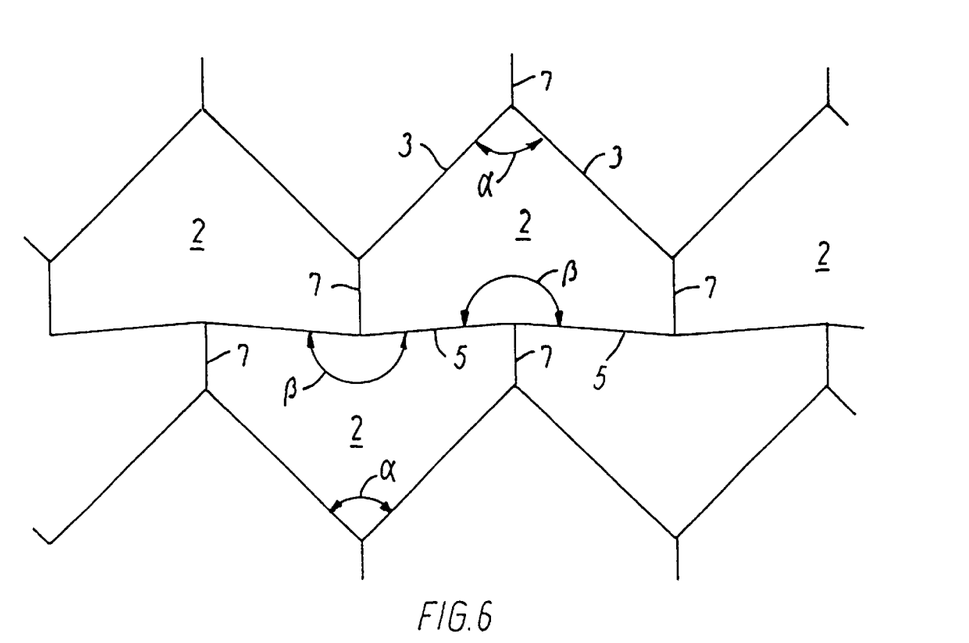
FIGS. 6 and 7 are outlines of two unfolded frame sections illustrating the effect of varying the angle between the two shorter frame sides.
Figure 7:
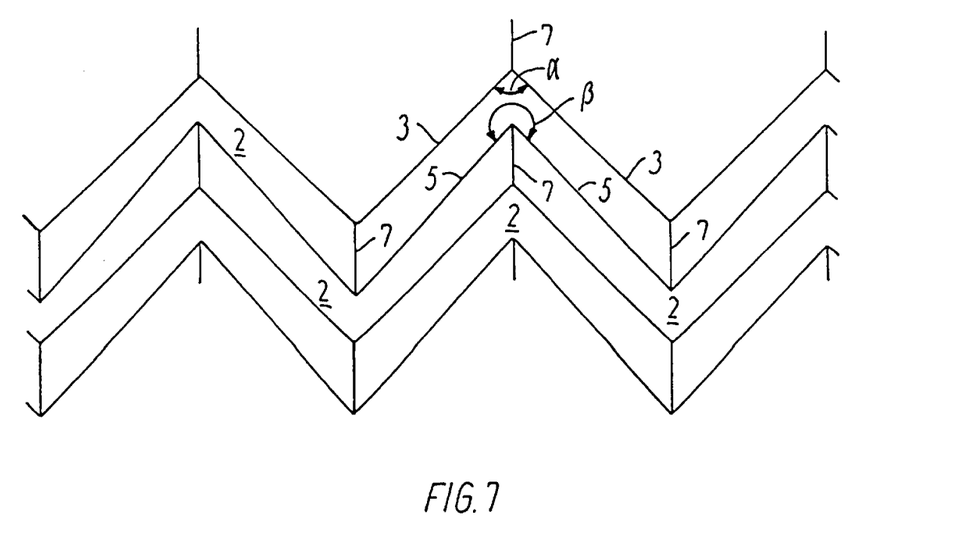

In a comparison between the two embodiments shown in FIGS. 6 and 7, the influence of the second angle β on the cell shape is seen when the cell width, the first angle and the length of the side sections 7 are kept unchanged in relation to the embodiment of FIG. 3. In FIG. 6, the second angle β is about 184°, and in FIG. 7 about 275°. In FIG. 6, the frame structure is open, and the shorter cell sides form slightly curved, annular bands giving the body 1 a high pressure rigidity. In FIG. 7, the frame structure is very dense and enables the body to over-expand heavily.

Figure 8:
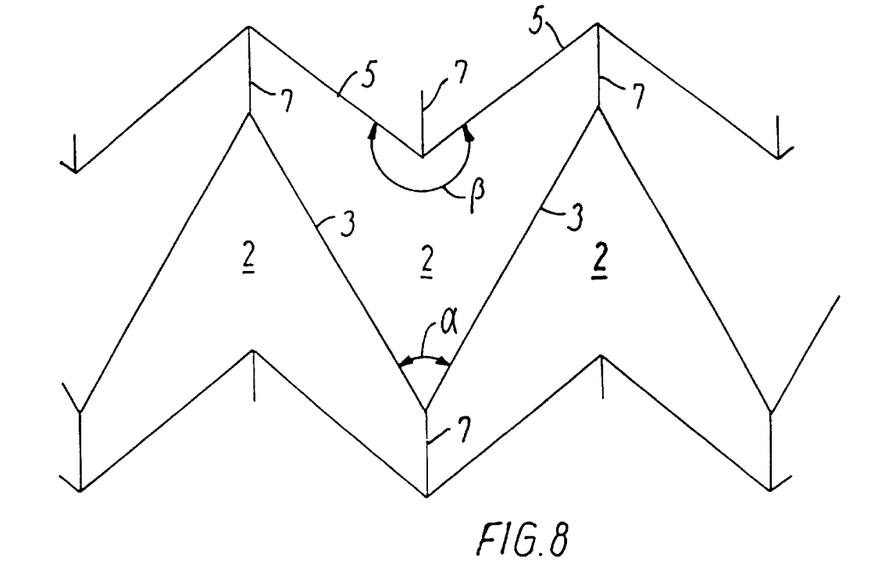
FIGS. 8 and 9 are corresponding outlines for illustration of the effect of varying the angle between the two longer frame sides.
Figure 9:
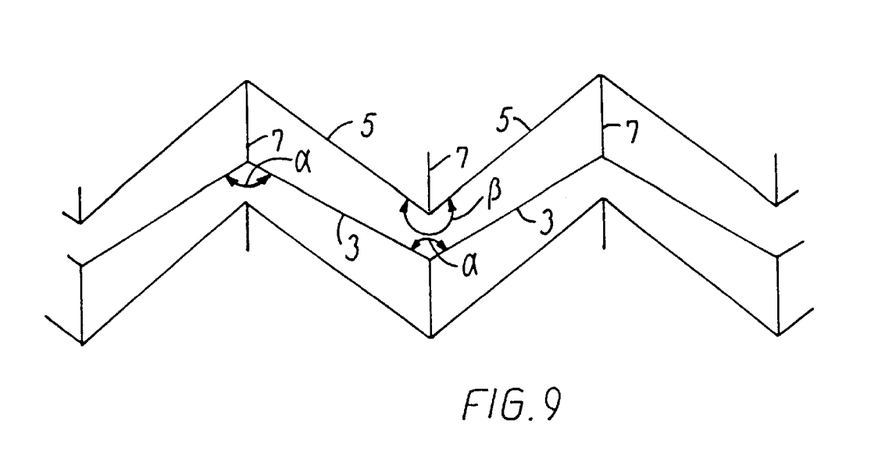

In a comparison between the two embodiments shown in FIGS. 8 and 9, the influence of the first angle on the cell shape is seen when the cell width, the second angle and the length of the side sections 7 are kept unchanged in relation to the embodiment of FIG. 3. In FIG. 8, the first angle is about 62°, while in FIG. 9 it is about 120°. In FIG. 8, the cells have a very open structure. In FIG. 9, the structure is very dense, but the amount of wire is also large in comparison to the length of the stent.

The stent material is preferably nitinol, which has excellent elastic properties and can tolerate large deformations. Alternatively, stainless steel, titanium, copper alloys, tantalum or other biologically compatible materials capable of maintaining the expanded state inside the vessel, or mixtures of such materials may be used. If the stent is balloon-expanded at the positioning in the vessel, stainless steel may be just as suitable as nitinol. It is also possible to use a synthetic material as the stent material, such as modified butadiene or another synthetic material with good resilient properties.

The cross-sectional area of the cell sides is chosen on the basis of the desired diameter, desired rigidity and the cell shape in the stent, a larger cross-sectional area being used at larger diameters, at a larger desired rigidity and/or at more open cells or lower cell number. When the frame shape shown in FIG. 3 is used for a stent for use in the Iliac, the stent may, for example, have a diameter of 8 mm, there may be four cells in each annular row, and the filament may, for example, be a nitinol wire with a diameter of 0.16 mm. A corresponding stent can be used in bile ducts, the lumen of which is reduced by tumors or fibrosis. Stents may also be used for expanding the oesophagus in patients suffering from malignant dysphagia, for expanding the urinary tracts or other body vessels. A very important field of application is stents for expanding constrictions in blood vessels or for maintaining expanded vasoconstrictions, such as in hard stenoses. The below list mentions examples of applicable stent diameters, etc., for different applications.

| Field of application | Stent diameter |
|---|---|
| Arteries | |
| Coronary | 2–4 mm |
| Iliac | 6–12 mm |
| Femoral | 6–12 mm |
| Renal | 6–12 mm |
| Carotid | 6–12 mm |
| Aortic aneurism | 15–30 mm |
| Veins | |
| Vena cava | 12–30 mm |
| Vena subclavia | 12–30 mm |
| Arteriovenous shunt endoprosthesis | 6–14 mm |
| TIPS (by-pass in liver) | 10–12 mm |
| Urology | |
| Ureteral | 4–7 mm |
| Urethral | 4–7 mm |
| Gastroenterology | |
| Esophageal | 18 mm at the middle |
| Biliary | 6–10 mm |
| Pancreatic | 2–3 mm |
| Thorax | |
| Bronchial | 15–20 mm |

The filament diameter or the thickness/width of the cell sides is adapted to the stent diameter, the cell sides being given less cross-sectional area at smaller stent diameters. The filament diameter may, for example, be in the interval of 0.06–0.40 mm.

Figure 10:
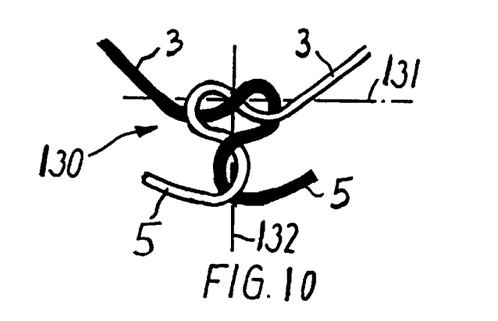
FIG. 10 is a top view of a particular manner of winding pairs of filaments at cell junctions.

When the tubular body is made of several filaments, these filaments may be wound about each other at the cell junctions in other manners than depicted in FIG. 3. In FIG. 10 the winding is made so as to produce a type of knot 130. At the cell junction the two filaments 3 and 5 are twisted one turn about each other about a twist axis 131 extending in a first direction and then the filaments are bent in direction of a second twist axis 132 extending at an angle, preferably at approximately 90° to said first direction, and are twisted at least one turn about each other. The first direction may preferably extends approximately in the circumferential direction of the tubular body and the second twist axis may then extend approximately in the longitudinal direction of the tubular body.

It is possible to supplement the stent with a covering on at least a part of the peripheral surface of the tubular body. The covering is impermeable to blood and may be a weave or a sheath of a suitably tight material, such as Dacron, PTFE or another suitable biocompatible material. The stent with the covering constitutes a graft which may be used as an artificial vessel. The use of a graft is well-known in the art and needs no further description. The stent according to the invention is particularly suitable for a graft because of its uniform properties and great ability to keep a patent vessel lumen despite considerable bending of or localized radial pressure loads on the graft.

What is claimed is:

1. An expandable endovascular stent comprising a flexible, tubular body (1) with a longitudinal axis, a wall of which is formed by interconnected, closed frame cells (2) arranged with at least two cells adjacent to each other in a circumferential direction, the frame cells (2) having at least two elongated, mutually converging cell sides, the body including filament-shaped frame material that transmits compressive forces in an axial direction of a filament extending continuously from one frame cell directly into an other frame cell following in a longitudinal direction, which stent is expandable from a radially compressed state into an expanded state having a larger diameter, wherein in the expanded state of the stent, the filament-shaped frame material in several of the frame cells (2) forms at least one of a heart-like shape and an arrowhead-like shape with at least two interconnected shorter cell sides (5) positioned opposite to and interconnected with the two mutually converging longer cell sides (3), and wherein the shorter cell sides (5) do not deform radially outward from the longer cell sides (3) upon radial expansion of the stent to its expanded state.

2. An expandable endovascular stent according to claim 1, wherein the heart-like shape includes a heart point, wherein the arrowhead-like shape includes an arrowhead, wherein at least one of the arrowheads and the heart points (4) face in the longitudinal direction of the body (1), and wherein an interval between two neighboring frame cells with a same orientation of the at least one of the arrowheads and the heart points (4) consists of a frame cell with an opposite orientation of at least one of the arrowhead and the heart point (4).

3. An expandable endovascular stent according to claim 2, wherein the frame cells (2) adjacent to each other in an annular row in the circumferential direction of the body (1) have alternatingly oriented at least one of the arrowheads and the heart points (4) and constitute a frame pattern repeated along the length of the body.

4. An expandable endovascular stent according to claim 1, wherein the two shorter cell sides (5) have substantially the same length, and that the two longer cell sides (3) have substantially the same length.

5. An expandable endovascular stent according to claim 1, wherein a first angle ($\alpha$) between the two longer cell sides (3) and facing into the cell is in the interval of 20–160° and wherein a second angle ($\beta$) between the two shorter cell sides (5) and facing into the cell is in the interval of 184–340°.

6. An expandable endovascular stent according to claim 5, wherein the longer cell sides (3) and the shorter cell sides (5) all form an angle of between 10° and 45° with the longitudinal direction of the body (1).

7. An expandable endovascular stent according to claim 6, wherein said first angle ($\alpha$) in the frame cells (2) is smaller in one area of the body (1) than in another area of the body.

8. An expandable endovascular stent according to claim 5, wherein the first angle ($\alpha$) is in the interval of 60°–120° and wherein the second angle ($\beta$) is in the interval of 210°–320°.

9. An expandable endovascular stent according to claim 6, wherein the longer cells sides (3) form an angle of between 40° and 45° with the longitudinal direction.

10. An expandable endovascular stent according to claim 1, wherein a first angle ($\alpha$) in the frame cells (2) is smaller in one area of the body (1) than in another area of the body.

11. An expandable endovascular stent according to claim 1, wherein a second angle ($\beta$) in the frame cells (2) is larger in one area of the body (1) than in another area of the body.

12. An expandable endovascular stent according to claim 11, wherein the second angle ($\beta$) is larger at end areas of the body.

13. An expandable endovascular stent according to claim 1, wherein at at least one end of the body (1), at least one of the shorter and longer cell sides (3, 5) of the frame cells (2) are of greater length and the frame cells (2) have a smaller angle ($\beta$) between the shorter cell sides (5) than at a middle of the body, whereby the body has a larger diameter at an end than at the middle.

14. An expandable endovascular stent according to claim 1, wherein the number of frame cells (2) in an annular row in the circumferential direction of the body (1) corresponds to a radius of the body measured in mm.

15. An expandable endovascular stent according to claim 1, wherein the body (1) is formed from at least one of a thin-walled tube.

16. An expandable endovascular stent according to claim 1, wherein the tubular body (1) is provided on at least part of its peripheral surface with a covering which is impermeable to blood.

17. An expandable endovascular stent comprising a flexible, tubular body (1) with a longitudinal axis, a wall of which is formed by interconnected, closed frame cells (2) arranged with at least two cells adjacent to each other in a circumferential direction, the frame cells (2) having at least two elongated, mutually converging cell sides, the body including filament-shaped frame material that transmits compressive force in an axial direction of a filament extending continuously from one frame cell directly into an other frame cell following in a longitudinal direction, which stent is expandable from a radially compressed state into an expanded state having a larger diameter, wherein in the expanded state of the stent, the filament-shaped frame material in several of the frame cells (2) forms at least one of a heart-like shape and an arrowhead-like shape with at least two interconnected shorter cell sides (5) positioned opposite to and interconnected with the two mutually converging longer cell sides (3), and wherein the body (1) is formed by several filaments (10, 11) constituting the shorter and longer cell sides (3, 5) and being wound about each other at adjacent ends of pairs of shorter and longer cell sides.

18. An expandable endovascular stent according to claim 17, wherein each filament (10, 11) has at least one of a stepped spiral-like course and a stepped wave-like course in the longitudinal direction of the body (1).

19. An expandable endovascular stent according to claim 18, wherein said first direction extends approximately in the circumferential direction of the tubular body and said second twist axis extends approximately in the longitudinal direction of the tubular body.

20. An expandable endovascular stent according to claim 17, wherein the tubular body (1) includes cell junctions where pairs of filaments (10, 11) are twisted one turn about each other about a twist axis extending in a first direction and at least one turn about each other about a second twist axis extending at an angle to said first direction.

* * * * *